United States Patent [19]

Kilbride, Jr. et al.

[11] Patent Number: 5,000,888
[45] Date of Patent: Mar. 19, 1991

[54] PROCESS FOR SPRAY DRYING RIBOFLAVIN TO PRODUCE A GRANULATE PRODUCT HAVING LOW BINDER CONTENT

[75] Inventors: Terence K. Kilbride, Jr., Bloomfield Hills; Rudolph E. Lisa, Grosse Ile, both of Mich.

[73] Assignee: BASF Corporation, Parsippany, N.J.

[21] Appl. No.: 527,458

[22] Filed: May 23, 1990

[51] Int. Cl.$^5$ .................. B29B 9/10; A61K 31/525
[52] U.S. Cl. .................................... 264/7; 264/12; 264/13; 514/251
[58] Field of Search ................... 264/5, 7, 12, 13; 544/251; 514/251

[56] References Cited

U.S. PATENT DOCUMENTS

| | | | |
|---|---|---|---|
| 3,959,472 | 5/1976 | Cannalonga et al. | 514/251 |
| 3,962,384 | 6/1976 | Cannalonga et al. | 264/7 |
| 4,486,435 | 12/1984 | Schmidt et al. | 514/251 |
| 4,605,666 | 8/1986 | Schmidt et al. | 514/960 |
| 4,868,180 | 9/1989 | Izuhara et al. | 514/251 |

*Primary Examiner*—Mary Lynn Fertig
*Attorney, Agent, or Firm*—Rupert B. Hurley, Jr.

[57] ABSTRACT

A method for producing a granulated riboflavin product comprises making a specific mixture of riboflavin, binder and water, followed by homogenizing the mixture and thereafter spray-drying the homogenized mixture so that granules are produced. The mixture has a relatively high vitamin and binder content but is reduced to a relatively low viscosity (via homogenization) so that spray drying can be performed.

13 Claims, No Drawings

PROCESS FOR SPRAY DRYING RIBOFLAVIN TO PRODUCE A GRANULATE PRODUCT HAVING LOW BINDER CONTENT

BACKGROUND OF THE INVENTION

The present invention pertains to spray drying processes, and more particularly to spray drying processes in which the major vitamin component in the resulting dry product is riboflavin. Prior to the present invention, spray-dried riboflavin processes and products have all involved relatively high amounts of binder (together with other components) therein, i.e., the amount of binder, etc. present approximated the amount of vitamin present. Although a 50% riboflavin product has been found acceptable for use in animal feed formulations, it is desirable to have a much higher vitamin content (i.e., even greater than 90 weight percent vitamin) for pharmaceutical and food applications. The process of the present invention enables the manufacturing of such a product while at the same time, unexpectedly enabling the production of a product having very desirable properties such as high flow rate and low dustiness and low electrostatic clumping and bridging.

Riboflavin is available as a fine powder of various purities (90-100%). This powder is clingy, dusty and highly electrostatic. This powder sticks to and fouls any process equipment with which it comes into contact. Furthermore the powder tends to bridge and clump during handling. There can be significant losses due to a buildup of the riboflavin particles on the processing equipment utilized in food, feed, and pharmaceutical industries. In addition, substantial labor must be expended to remove the adhering material from the equipment.

Prior to this invention, in the pharmaceutical and food industries, ungranulated high concentration riboflavin powders (90-100 weight percent riboflavin) have been used in powder form. However, as noted above, this powder presents flowability, handling, and processing problems. The method of the present invention enables the production of a 90-100 weight percent granulated riboflavin product which has heretofore unachieved flowability characteristics. Furthermore, the process of the present invention enables the production of such a product through the highly desirable and efficient method of spray drying.

The closest related art known to the inventors consists of the following U.S. Pat. Nos.: 4,868,180, 3,962,384, 4,486,435, and European patent application 0,219,276. Although this art is the closest art of which the inventors are aware, none of this art describes spray drying processes for making a high vitamin content (i.e., at least 75 weight percent riboflavin)/low binder product (i.e., below 25 weight percent of binder in the spray dried particulates). Furthermore, none of this art describes any process for producing granule particle sizes with a geometric mean of from about 50 to about 300 microns and wherein the standard deviation of the particle sizes is from about 0 to about 3. In other words, the process of the present invention is the first process for making a spray-dried, granulated riboflavin product having a high riboflavin content. Furthermore, in addition to the high riboflavin content, the process results in the production of spray-dried particulates which have a relatively large particle size. Achieving the large particle size in combination with the high riboflavin content has proven to be difficult. Difficulties were encountered in that in order to make this relatively large particle size, it was necessary to utilize proportionally less water in the mixture being fed into the spray dryer chamber. However, the use of less water in the mixture results in a mixture having a substantially increased viscosity. This mixture cannot be sprayed unless the viscosity is reduced. However, the inventors of the present invention have unexpectedly found that if the mixture is thoroughly homogenized (rather than merely mixed), the viscosity will be reduced to a level at which the "homogenizate" (i.e., homogenized mixture which is homogeneous) is spray-dryable while containing only a relatively small concentration of water, which in turn permits the production of large particle size, high riboflavin content spray-dried granules.

The '384 and '435 patents are directed at compositions which have a binder present in an amount of around 50 weight percent. The use of large amounts of binder (i.e., amounts greater than 25 weight percent, based on total dry product weight) enables the substantially complete granulation of the riboflavin, whereas substantially complete granulation (i.e., less than 10 weight percent ungranulated riboflavin) is much more difficult to achieve if less than 25 weight percent binder is utilized.

U.S. Pat. No. 4,868,180 describes a 90-99% vitamin B granulate which is made by conventional fluid bed granulation, followed by pulverizing the resulting granulate in a Fitz mill. The '180 patent nowhere refers to spray drying. The '180 patent nowhere refers to product yield, (i.e., amount of material lost or adhering to equipment surfaces) completeness of granulation (i.e., level of fines). In contrast to the '180 patent, the process of the present invention is related solely to a spray drying process, as opposed to the fluid bed process described in the '180 patent.

European application 0,219,276 is an equivalent of the '180 patent, discussed above.

BRIEF SUMMARY OF THE INVENTION

The present invention is a method which employs spray drying for producing a granulated riboflavin product. The granulated riboflavin product comprises substantially dry granules, the granules being comprised of riboflavin in an amount of from about 75 weight percent to about 99.5 weight percent. In the following brief description, all parts referred to are parts by weight.

First, from about 10 parts to about 50 parts riboflavin are combined with from about 0.5 parts to about 15 parts of a binder and from about 50 to about 75 parts water. The binder is at least one member selected from the group consisting of pregelatinized starches, water-soluble celluloses, and water-soluble high polymers However, the amount of binder utilized is such that a ratio of parts of binder to parts of riboflavin is from about 1:3 to 1:200. The combination of vitamin, binder, and water together make up a mixture. However, the mixture of vitamin, binder, and water must be such that the amount of water in the mixture is from about 40 weight percent to about 75 weight percent.

Second, the mixture is homogenized so that the mixture is substantially homogeneous and so that the mixture has a viscosity of from about 1 centipoise to about 4,000 centipoise, whereby a homogenized mixture is produced.

Third, the homogenized mixture is spray-atomized into a spray dryer chamber whereby droplets are produced. This spraying is carried out so that an average droplet size is produced wherein upon drying substantially dry granules are produced, the granules having a geometric mean particle size of from about 50 microns to about 300 microns with a standard deviation of from about 0 to about 3.

Fourth, after spraying the homogenized mixture into the spray dryer chamber whereby droplets are formed, the droplets are dried in the spray drying chamber until spray-dried granules are formed, the spray-dried granules having a water content of from about 0.1 weight percent to about 4 weight percent, based on granule weight.

It is an object of the present invention to provide a process for making a spray-dried vitamin product.

It is a further object of the present invention to provide a process for making a spray-dried riboflavin granulate product wherein the riboflavin content exceeds 75 weight percent of the product.

It is a further object of the present invention to provide a process for producing a spray-dried pharmaceutical grade riboflavin granulate product.

It is a further object of the present invention to provide a process for making a spray-dried riboflavin product having less than 25 weight percent of a binder therein.

It is a further object of the present invention to provide a process for making a spray-dried riboflavin product having exceptional flow characteristics.

It is a further object of the present invention to enable the production of a spray-dried riboflavin product having a large particle size.

It is a further object of the present invention to enable the production of a spray-dried riboflavin product having low dustiness and low electrostatic cling.

It is a further object of the method of the present invention to enable the production of a spray-dried riboflavin product in which there is both a riboflavin content of greater than 75 weight percent and wherein the particles are of a relatively uniform and relatively large size, in comparison with other spray-dried products.

DETAILED DESCRIPTION OF THE PREFERRED EMBODIMENTS

The present invention pertains to a process for making a spray-dried riboflavin granulate. A binder is utilized in the process of the present invention. The binding agent is a water-soluble binder or a binder soluble in an organic solvent. The water-soluble binder may be a pregelatinized starch, water-soluble cellulose, a water-soluble high polymer, etc. A pregelatinized starch is a starch prepared by heating a dispersion of starch in water or a dry starch obtained by drying the same. The pregelatinized starch is exemplified by pregelatinized corn starches, pregelatinized potato starches, and pregelatinized modified starches [e.g., those described in Code of Federal Regulations (U.S.A.) §121, 1031a, b, c, d, e, f, g and h]. Furthermore there are pregelatinized dry commercial products such as Amycol C (Nichiden Chemical Company, Japan), Amylox (Nihon Corn Starch Company, Japan), Pre-Gel (Hublinger Company, U.S.A.), or Instant Cleargel (National Starch Company, U.S.A.).

Examples of water-soluble celluloses include, for example, hydroxypropylcellulose, hydroxymethylcellulose, hydroxypropylmethylcellulose, carboxymethylcellulose, methylcellulose, etc. The water-soluble high molecular weight compounds (water-soluble high polymers) are exemplified by polyvinylpyrrolidone, polyvinyl alcohol, dextrin, gum arabic, gelatin, polydextrose, etc.

Binding agents soluble in organic solvents may be, for example, cellulose derivatives soluble in organic solvents, such as cellulose acetate phthalate, hydroxypropylmethylcellulose phthalate, ethylcellulose, etc. However, water-soluble binders (especially water-soluble celluloses) are preferred over binding agents soluble in organic solvents.

The solvent used to prepare a solution containing a binding agent or spraying includes water and organic solvents, for example lower alcohols (e.g., methylalcohol, ethylalcohol, isopropylalcohol, etc.) as well as ketones (e.g., acetone, etc.).

It is preferred that the binder utilized in the process is at least one member selected from the group consisting of hydroxypropyl methylcellulose, hydroxymethylcellulose, polyvinylpyrrolidone, and gum arabic. It is most preferred that the binder is hydroxypropylmethylcellulose.

The first step in the process of the present invention is to combine the riboflavin with the binder and water. For purposes of the process of the present invention, the amount of binder utilized must always be such that a ratio of the parts of binder to the parts of riboflavin is less than 1:3. So long as this ratio is satisfied, in general the mixture of riboflavin, binder, and water can be made utilizing riboflavin in an amount of from about 10 parts by weight to about 50 parts by weight, together with from about 0.5 parts to about 15 parts binder, together with from about 50 to about 75 parts water. However, the mixture of riboflavin, binder, and water must always be such that the amount of water in the mixture is from about 40 weight percent to about 75 weight percent. All these parts are parts by weight. Preferably, the mixture is made by combining from about 25 parts to about 40 parts riboflavin with from about 1.25 to about 13.3 parts binder together with from about 60 to about 70 parts water. Preferably, the ratio of the parts of binder to the parts of riboflavin is less than 1:5. Most preferably, the mixture is produced by combining about 33 parts riboflavin with about 1.75 parts binder and about 64 parts water. Most preferably, the ratio of the parts of binder to the parts of riboflavin is about 1:24.

Once the mixture is produced by combining the ingredients as described above, the mixture is then homogenized so that the mixture is substantially uniform (i.e., homogeneous). As used herein, the term "homogenize" refers to any process wherein a liquid or mixture of liquid and solid is subjected to high sheer forces. An example of equipment capable of imparting this type of sheer is a Gifford-Wood homogenizer manufactured by Greerco Corporation of Hudson, N.H. It has been found that merely mixing the mixture under conditions of low sheer will not result in a homogenized mixture. Furthermore, it has been found that by homogenizing the mixture (i.e., the use of high shear) the viscosity of the mixture is reduced substantially. It is only by reducing the viscosity of the mixture that the mixture is rendered suitable for spray drying operations. That is, the ratio of ingredients required in the process will, without homogenization, not be suitable for spray drying because the mixture will be too viscus to undergo pumping via conventional means, and atomization. As a result, the homogenization step of the present invention is critical in that it enables a lowering of the viscosity of the mixture to a point at which the mixture is suitable for spray drying operations. Generally, the viscosity of the homogenized mixture should be from about 1 centipoise to about 4,000 centipoise. Preferably, the homogenized mixture has a viscosity of from about 200 centipoise to about 500 centipoise. Most preferably, the viscosity of the homogenized mixture is from about 300 centipoise to about 400 centipoise.

Once the homogenized mixture is produced, the next step is to spray dry the homogenized mixture The process of spray drying is carried out by spray-atomizing the homogenized mixture into a spray dryer chamber The spray-atomizing may be carried out, for example, by pumping the homogenized mixture into a rotating spray nozzle or, alternatively, by pumping the homogenized mixture (under very high pressures) into a fixed-position atomizing nozzel. The preferred method of spray-atomizing is to pump the homogenized mixture into a rotating wheel type of sprayer. In the process of the present invention, the spray-atomizing must, in general, be carried out so that the droplets formed will, upon drying, solidify into spray-dried particulates having a geometric mean particle size of from about 50 microns to about 300 microns, with the particle size distribution exhibiting a standard deviation of from about 0 to about 3. Preferably the spray drying is carried out so that the droplets, upon drying, form spray-dried particulates having a geometric mean particle size of from about 50 microns to about 200 microns, with a standard deviation of from about 1 to about 2.2. Most preferably, the spray drying is carried out so that the droplets, upon drying, form solid particulates having a geometric mean particle size of about 80 microns, with a particle size distribution exhibiting a standard deviation of about 1. In order to achieve a geometric mean particle size and a particle size distribution within the scope of the process of the present invention, it is necessary to utilize a proper: (1) surface speed for the rotating spray nozzle; (2) air flow rate through the spray dryer chamber; and (3) air temperature within the spray dryer chamber. Without utilizing the proper conditions within the spray dryer chamber, the particles will be too small (hence dusty, with poor flow characteristics) and/or the droplets may fail to adequately dry before contacting either each other or the walls of the spray dryer. In general, the surface speed of the rotating wheel spray nozzle is from about 15,000 to about 60,000 feet per minute. Preferably the surface speed of the rotating spray wheel is from about 20,000 feet per minute to about 55,000 feet per minute. Most preferably the surface speed of the rotating spray wheel is from about 25,000 feet per minute to about 28,000 feet per minute. The higher the surface speed of the rotating spray wheel, the finer the particles produced, because the corresponding centrifugal force produced is also higher. The inlet air temperature flowing into the spray dryer chamber is generally from about 125° C. to about 400° C. Preferably the inlet air temperature is from about 150° C to about 300° C. Most preferably the inlet air temperature is from about 175° C. to about 225° C. As is well known in the art of spray drying, the higher the inlet air temperature the faster the drying occurs. In the process of the present invention, optimally the temperature is high enough to dry the droplets to a degree of dryness whereby the resulting particulates neither adhere to one another nor to the surfaces of the spray dryer or other equipment. Furthermore, the temperature is not so high that any of the components within the droplet or particulates are thermally degraded.

Once the homogenized mixture is sprayed into the dryer chamber so that droplets are formed, the droplets are then dried in the spray dryer chamber. This drying step, for the most part occurs very quickly, due to the high surface area of the droplets together with a relatively high rate of airflow, which air is hot and dry. In general, the drying should be carried out so that the moisture present in the final product (i.e., the spray-dried particulates) is from about 0.1 weight percent to about 4 weight percent. Preferably, the spray-dried particulates have a moisture content of from about 0.1 weight percent to about 0.75 weight percent. Most preferably, the spray-dried particulates have a moisture content of from about 0.1 weight percent to about 0.5 weight percent.

The process of the present invention pertains to a method for making a spray-dried riboflavin granulate having a "low binder content". The phrase low binder content, as utilized herein, refers to the ratio of vitamin to binder which are combined in the first step of the process. In general, this ratio is from about 1:3 (binder:riboflavin) to about 1:200 (binder:riboflavin). Preferably, the weight ratio of binder to riboflavin is from about 1:10 to about 1:200. Most preferably the weight ratio of binder to riboflavin is around 1:19 (binder:riboflavin).

An optional step in the process of the present invention is the coating of the droplets with a particulate absorbent material which coats the outside of the droplets, improving the flowability of the resulting particulates, as well as decreasing any tendency of droplets to adhere to one another or the walls of the dryer chamber. The absorbent particles have been described in U.S. Pat. Nos. 4,486,435 and 3,962,384. The absorbents fall into two groups, with each of the above patents describing one of the groups. First, U.S. Pat. No. 3,962,384 describes an ultra-fine absorbent, which in general includes silicic acid, silicon dioxide or various silicates, along with other materials which may be equally effective due to physical properties as opposed to chemical composition. These absorbents are described as being insoluble in cold water, resistant to wetting by water, having an appreciable capacity to absorb and/or adsorb water and oil (i.e. an oil absorption capacity of from about 150 to about 400 lbs. per 100 lbs. absorbent). Furthermore, they are free-flowing, they do not develop static electricity, and they have a particle size range of from about 2 microns to about 16 microns as well as a surface area of from about 175 to about 360 $m^2/gm$. Examples of these absorbents include silicic acid, silicas, alkali metal silicates, magnesium carbonate, kaolin clays, dicalcium phosphate, tricalcium phosphate and the like. A preferred absorbent from this group is silicic acid, a white amorphous powder, insoluble in water and having the empirical formula $SiO_2 \cdot x\ H_2O$.

The second group of absorbents, i.e. those described in U.S. Pat. No. 4,486,435, are termed hydrophobic silica particles. Hydrophobic silicas are a special form of silica made from silica gel, precipitated silica or fumed silica by standard treatments known in the art. Such treatments involve the use of silanes or polysiloxanes to provide the desired hydrophobicity. It is also known to provide hydrophobic silicas by treatment of silica gel, precipitated silica or fumed silica with esterified coatings derived from high boiling alcohols. Other fine particle size materials characterized as hydrophobic may be as effective as the hydrophobic silicas since it is not so much the chemical composition of the fine particle size coating composition which is critical to spray drying processes, but rather the physical properties of the absorbent which are critical to the spray drying processes. Generally, the hydrophobic silica coating materials are substantially insoluble in water, having a primary particle size of from about 0.01 microns to about 0.04 microns, and having a surface area of from about 90 to about 130 square meters per gram. As can be seen in comparing the first group of silicas with the second group of silicas, the second group has a significantly smaller particle size as well as a special hydrophobic character, in comparison with the first group of absorbents.

In the process of the present invention, it is most preferred to utilize an absorbent as described in the second group, i.e. as described in U.S. Pat. No. 4,486,435. However, in general, any of the absorbents from either group described above may be utilized in the process of the present invention. Preferably, however, the absorbent is a member selected from the group consisting of silicic acid, silica gel, an alkali metal silicate, magnesium carbonate, kaolin clay, dicalcium phosphate, or a hydrophobic silica having a primary particle size of from about 0.01 microns to about 0.04 microns, (the hydrophobic silica surface area of about 90 to about 130 square meters per gram).

The absorbent is added to the spray dryer chamber during the spraying process. The absorbent, being of a very small particle size, is atomized by the turbulent airflow through out the spray-dryer chamber. The atomized absorbent coats the surface of the droplets There are various means of addition of the absorbent into the spray-dryer chamber. It is most preferred to meter the absorbent into the chamber through a top inlet valve positioned above the atomizer wheel. However, the absorbent may be metered into the spray dryer chamber at virtually any location therein, and the absorbent need not be forcefully "sprayed" into the spray dryer chamber, but rather may be merely fed into the chamber at any substantially uniform desired rate. In general, the absorbent should be added to the spray dryer chamber at a rate so that the resulting spray dried particulates comprise absorbent in an amount of from about 0.5 weight percent to about 5 weight percent Preferably, the particulate absorbent is metered into the spray dryer chamber at a rate so that the resulting spray dried particulates comprise absorbent in an amount of from about 0.5 weight percent to about 2 weight percent Most preferably, the absorbent is metered into the spray dryer chamber at a rate so that the resulting spray dried particulates comprise absorbent in an amount of from about 0.5 weight percent to about 1 weight percent.

FLODEX METHOD FOR FLOWABILITY DETERMINATION

Flowability was measured using a Flodex ® Powder Flowability Index Test Instrument, Model 211, purchased from Hanson Research Corporation, 19727 Bahama Street, P.O. Box 35, Northridge, Calif., 91328. The Flodex ® apparatus presents a sample method for repeatable determination of powder flow characteristics. The Flodex ® device operates based upon the ability of a powder to fall freely through a hole in a plate. As used herein the Flowability Index was calculated by dividing 1000 by the orifice diameter in millimeters. For example, powder which will pass through an orifice diameter 4 millimeters in diameter, but not smaller, has a Flowability Index of 250.

The setup an operation of the Flodex ® Powder Flowability Index Test Instrument is thoroughly described in the Instruction Manual for the Flodex ® Model 211 apparatus, this Instruction Manual being hereby incorporated by reference. In addition, below is briefly described the method of determining flowability when using this device.

First, a 50 gram sample of the powder to be tested was used to fill the receptacle cylinder (funnel) to within about a centimeter from the top of the cylinder The powder was carefully loaded into the funnel so that there was no packing of the powder within the funnel, (of course, packing would have caused a loss of flowability of the powder). After the loading of the funnel, a minimum of 30 seconds was allowed to pass before the test was begun, in order to allow the possible formation of any flocculi. To begin the test, the release lever was slowly moved forward to drop open the hole closure, without vibration. If the test was positive, the open hole was visible from the top when looking down to see the hole at the bottom The Flodex ® device should not be tapped or shaken during the test. If the test results were positive, the test was repeated with a smaller orifice diameter, until the orifice was of such a smaller diameter that a negative result (i.e., lack of flow) was achieved.

The Flodex ® apparatus is supplied with nineteen disks, from 4 to 32 millimeter hole diameters in one millimeter increments from 4 to 10 millimeters and in 2 millimeter increments for disks having a hole greater than 10 millimeters in diameter. In addition to these disks, the Inventors herein had 2 additional disks fabricated, one with a 2 millimeter hole, the other with a one millimeter hole. These two additional disks provided a means for determining flowability indexes of 500 and 1000, respectively.

In general, the granulated riboflavin product of the present invention should have a Flodex (i.e., flowability index) of from about 75 to about 750, and preferably the Flodex is from about 100 to about 500. Most preferably, the Flodex is from about 150 to about 350.

EXAMPLE 1

This example illustrates a method for the preparation of a free flowing, spray-dried, static-free riboflavin powder containing over 75% by weight riboflavin in the spray-dried powder.

In a five gallon tank containing 66.18 parts of water were heated to 40° C. by a hot plate. 1.61 Parts of water-soluble hydroxypropylmethylcellulose (sold under the trade name "Methocel E-5") were then dissolved into the hot water, with stirring Thereafter, 32.21 parts by weight of a commercially available riboflavin powder having a purity of 99% to 100% were then added to the solution of water and hydroxypropylmethylcellulose, to yield a yellow/orange suspension of riboflavin. This slurry was then homogenized using a Gifford-Wood homogenizer (manufactured by Greerco). The homogenization was continued for approximately 15 minutes, resulting in the reduction of the viscosity to about 385 centipoise.

Utilizing a laboratory size spray-drying apparatus, having a variable-speed atomizing wheel, feed tanks, and pump, the previously prepared homogenized riboflavin suspension was metered to the atomizing wheel. The atomizing wheel (a slotted wheel obtained from Niro Atomizers, Inc., 9165 Rumsey Road, Columbia, Md., as used in utility dryer Model IV) was operated at 21,000 rpms, a centrifugal speed of about 8,000 meters per minute. The inlet air temperature flowing into the spray dryer chamber was about 200° C., and the outlet air temperature was about 100° C. The riboflavin suspension was fed into the spray atomizing wheel at a rate of about 125 grams per minute.

The resulting riboflavin powder was an orange, free-flowing, static-free powder having a bulk density of 0.43 grams per cubic centimeter with a geometric mean particle size of about 58 microns and a log standard deviation of about 1.5 microns. Furthermore, the powder had a flowability index (as measured by the Flodex method) of at least 333. [A flowability index greater than 100 is indicative of excellent flowability.] This powder mixed well in flour premixes and produced directly compressible tablets with the hardness of 12 scu. The final product (i.e., upon completion of drying) was made up of about 94 weight percent riboflavin, 5 weight percent binder, and 1 weight percent water.

EXAMPLE 2

In a five gallon tank, 72 parts of water were heated to 40° C., 1.45 parts of water-soluble hydroxypropylmethylcellulose (sold under the trade name "Methocel E-5") were dissolved into the hot water, with stirring. Thereafter, 26.55 parts by weight of a commercially available riboflavin powder having a purity of 99% to 100% were added to the solution to yield a yellow-/orange suspension of riboflavin. This suspension was then homogenized using a Gifford-Wood homogenizer (manufactured by Greerco). The homogenization was carried out for approximately 15 minutes in order to reduce the viscosity. The final viscosity of the suspension was about 200 centipoise. The now homogenized riboflavin suspension was metered into the atomizing wheel of a laboratory size spray-drying apparatus, the apparatus having a variable speed atomizing wheel, feed tanks, and pump. The atomizing wheel was operated at 35,000 rpm, with a centrifugal speed of about 5,600 meters per minute The spray drying apparatus had an inlet temperature of about 200° C. and an outlet temperature of about 120° C.

The resulting spray-dried riboflavin powder exhibited poor flowability, and contained a great deal of static cling, and had a bulk density of 0.23 grams per cubic centimeter. The geometric mean particle size of this powder was about 41 microns, with a log standard deviation of from about 1.5 microns The flowability index, as measured by the Flodex method, was found to be about 50, i.e., indicative of poor flowability. The low flowability is an indication that this powder would perform poorly in tableting and flour premix tests The low flowability present in the product produced in this example is believed to be due to the small geometric mean particle size. The product was made up of about 94.5 weight percent riboflavin, 5.0 weight percent binder, and 0.5 weight percent water.

EXAMPLE 3

In a 750 gallon tank, 1.68 parts of water-soluble hydroxypropylmethylcellulose, sold under the trade name "Methocel E-5" were added to66.45 parts of water, with the hydroxypropylmethylcellulose being dissolved into the hot water, with stirring Thereafter, 33.55 parts (by weight) of a commercially available riboflavin powder having a purity of 99% to 100% were added to the mixture to yield a yellow/orange suspension of riboflavin. This suspension was then homogenized with a Gifford-Wood homogenizer. After homogenization was finished, the suspension had a viscosity of about 350 centipoise.

The riboflavin suspension was then metered into the atomizing wheel within a commercial spray dryer, the spray dryer having a variable speed atomizing wheel, feed tanks, and pump. The variable speed atomizing wheel was operated at about 8,000 rpm, a centrifugal speed of about 5,110 meters per minute. The spray dryer had an inlet air temperature of about 232° C. and an outlet air temperature of about 90° C.

The resulting riboflavin powder was a free-flowing, static-free powder having a bulk density of 0.37 grams per cubic centimeter with a geometric mean particle size of about 1.72 microns and a log standard deviation of about 1.5 microns. The flowability index, as measured by the Flodex method, was found to be equal to or greater than 333. This powder mixed well in flour premixes and produced directly compressible tablets with a hardness of 12.0 scu. The product was made up of about 94.6 weight percent riboflavin, 5 weight percent binder, and 0.4 weight percent water.

EXAMPLE 4

This example illustrates the positive effective produced by hydrophobic silica on the flowability of the product.

A riboflavin slurry was prepared and sprayed using the conditions outlined in Example 3, except that a silica cloud was maintained within the spray-dryer by screw feeding a hydrophobic synthetic silica, sold under the trademark "Aerosil R-972", so as to provide a coating on the spray-dried droplets This silica coating ultimately constituted between 1 and 2 weight percent of the total weight of the resulting spray-dried riboflavin powder.

The resulting riboflavin powder was very similar in particle size distribution and bulk density to the powder produced by Example 3. The powder was free-flowing, static-free, and had a bulk density of 0.37 grams per cubic centimeter with a geometric mean particle size of about 170 microns and a log standard deviation of about 1.0 microns. The difference between the product of Example 4 and the product of Example 3 was the flowability index. The powder produced with 1% hydrophobic silica had a flowability index of about 500, which was significantly greater than the flowability value measured for the powder produced in Example 3. The powder produced according to Example 4, mixed well in flour premixes and produced direct compression tablets with a hardness of 15.5 scu. The product was made up of about 94.6 weight percent riboflavin, 4.0 weight percent binder, 0.4 weight percent water, and 1.0 weight percent absorbent (i.e., hydrophobic silica).

EXAMPLE 5

This example illustrates the necessity of homogenizing the riboflavin, binder and water slurry if a spray-dried granulate is being produced.

In a five-gallon tank containing 66.18 parts of water heated to 40° C. by a hot plate, and 1.61 parts of water-soluble hydroxypropyl methylcellulose (sold under the trade name "Methocel E-5") were dissolved into the hot water by stirring with a "Lightnin" brand mixer with a 3.5 inch marine prop blade. Thereafter, 32.21 parts by weight of a commercially available riboflavin powder, having a purity of 99% to 100%, were added to the mixture, while stirring with the Lightnin mixer, to yield a yellow/orange suspension of riboflavin. The slurry had the consistency of a paste, and its viscosity was in excess of 8,000 centipoise. In this form the slurry was not suitable for spray drying because this paste could not be pumped or, more importantly, atomized using conventional spray drying equipment.

The slurry was then homogenized, using a Gifford-Wood homogenizer, for approximately 15 minutes This reduced the viscosity to 385 centipoise. This slurry was then spray dried under the conditions present in Example 1. The resulting spray-dried granulate was the same as the granulate described in Example 1.

The embodiments of the invention in which an exclusive privilege or property is claimed are defined as follows:

1. A method for producing a granulated riboflavin product which comprises substantially dry granules, the granules being comprised of riboflavin in an amount of from about 75 weight percent to about 99.5 weight percent, the method comprising the steps of:

A. Combining:

(1) from about 10 parts to about 50 parts riboflavin, with (2) from about 0.5 parts to about 15 parts of a binder which has at least one member selected from the group consisting of pregelatinized starches, water-soluble celluloses, and water-soluble high polymers, wherein an amount of binder utilized is such that a ratio of parts of binder to parts of riboflavin is from about 1:3 to about 1:200, (3) from about 50 parts to about 75 parts water, whereby a mixture is produced, and wherein the amount of water in the mixture is from about 40 weight percent to about 75 weight percent; and B. homogenizing the mixture so that the mixture is substantially homogeneous and so that the mixture has a viscosity of from about 1 centipoise to about 4,000 centipoise, whereby a homogenized mixture results; and C. spray-atomizing of the homogenized mixture into a spray dryer chamber to produce droplets, the droplets being sprayed in a manner so that an average droplet size is produced wherein upon drying substantially dry granules are produced, the granules having a geometric mean diameter of from about 50 microns to about 300 microns with a standard deviation of from about 0 to about 3; and D. drying the droplets in the spray drying chamber until spray-dried granules are formed, the granules having an ultimate water content of from about 0.1 weight percent to about 4 weight percent, based on granule weight.

2. A method as described in claim 1 wherein from about 25 parts to about 40 parts of riboflavin are combined with from about 0.125 parts to about 13.3 parts of the binder and from about 60 to about 70 parts water.

3. A method as described in claim 2 wherein the viscosity of the mixture is from about 200 centipoise to about 500 centipoise.

4. A method as described in claim 1 wherein air flowing into the spray dryer has a temperature from about 125° C. to about 400° C.

5. A process as described in claim 2 wherein air flows into the spray dryer at a temperature of from about 150° C. to about 300° C.

6. A method as described in claim 2 wherein the droplets are dried to a moisture content of from about 0.1 weight percent to about 0.75 weight percent, based on droplet weight.

7. A method as described in claim 2 wherein the spraying of the droplets is carried out so that the geometric mean diameter of the resulting particulates is from about 50 microns to about 200 microns, with a standard deviation of from about 1 to about 2.2.

8. A method as described in claim 1 wherein during the spraying of the homogenized mixture into the spray dryer chamber, there is a simultaneous addition of an effective amount of a dry particulate absorbent into the spray dryer chamber, the absorbent being at least 1 member selected from the group consisting of, silicon dioxide, silicas, hydrophobic silica, silicic acid, silica gel, an alkali metal silicate, magnesium carbonate, kaolin clay, dicalcium phosphate and tricalcium phosphate.

9. A method as described in claim 8 wherein the average particle size of the particular absorbent is from about 0.01 microns to about 16 microns.

10. A method as described in claim 8 wherein the particulate absorbent is added to the spray dryer at a rate so that the droplets, upon drying, comprise particulate absorbent in an amount of from about 0.5 weight percent to about 5 weight percent, based on the total weight of the sprayed particulate.

11. A method as described in claim 2 wherein during the spraying of the homogenized mixture into the spray dryer chamber there is simultaneously a particulate absorbent metered into the spray dryer chamber, the particulate absorbent being a hydrophobic silica having a primary particle size of from about 0.01 microns to about 0.04 microns.

12. A method as described in claim 11 wherein the particulate absorbent is metered into the spray dryer chamber at a rate so that the resulting sprayed particulates, upon drying, comprise the particulate absorbent in an amount of from about 0.5 weight percent to about 2 weight percent, based on the weight of the dry sprayed particulate.

13. A method for producing a vitamin product, the method comprising the steps of:

A. combining:

(1) about 33 parts of riboflavin, and (2) about 1.75 parts hydroxypropyl methylcellulose, and (3) about 64 parts water, whereby a mixture is produced; and B. homogenizing the mixture so that the mixture is substantially uniform and so that the mixture has a viscosity of from about 300 centipoise to about 400 centipoise, whereby a homogenized mixture results; and C. spraying the homogenized mixture into a spray dryer chamber so that upon drying the droplets whereby spray dried particulates are formed, the particulates have a geometric mean particle size of about 80 microns, with a standard deviation of about 1; and D. metering an ultra fine hydrophobic silica absorbent into the spray dryer chamber, the absorbent being metered into the spray dryer chamber, during the spraying of the homogenized mixture, at a rate so that the resulting spray-dried particulates comprise absorbent in an amount of from about 0.5 weight percent to about 1 weight percent, based on the total weight of the spray dried particulates.

* * * * *